(12) United States Patent
Sheppard et al.

(10) Patent No.: US 7,304,090 B2
(45) Date of Patent: Dec. 4, 2007

(54) INHIBITION OF THE CYSTIC FIBROSIS TRANSMEMBRANE CONDUCTANCE REGULATOR CHLORIDE CHANNEL

(75) Inventors: David Noel Sheppard, Bristol (GB); Zhiwei Cai, Bristol (GB)

(73) Assignee: The University of Bristol, Bristol (GB)

( * ) Notice: Subject to any disclaimer, the term of this patent is extended or adjusted under 35 U.S.C. 154(b) by 0 days.

(21) Appl. No.: 10/332,945

(22) PCT Filed: Jul. 12, 2001

(86) PCT No.: PCT/GB01/03154

§ 371 (c)(1),
(2), (4) Date: Jul. 14, 2003

(87) PCT Pub. No.: WO02/05794

PCT Pub. Date: Jan. 24, 2002

(65) Prior Publication Data

US 2004/0092578 A1 May 13, 2004

(30) Foreign Application Priority Data

Jul. 13, 2000 (GB) .................................. 0017084.5

(51) Int. Cl.
*A61K 31/35* (2006.01)
(52) U.S. Cl. ..................................................... 514/454
(58) Field of Classification Search ................. 514/454
See application file for complete search history.

(56) References Cited

U.S. PATENT DOCUMENTS 6,331,286 B1 * 12/2001 Dees et al. ................. 424/1.85

FOREIGN PATENT DOCUMENTS

WO     WO 96/18101     6/1996

OTHER PUBLICATIONS

CAS registry No. 18472-87-2 Phloxine B.*
Schultz et al. "Pharmacology of CFTR chloride channel activity," Physiological Reviews, 1999, vol. 79, suppl. No. 1, pp. s109-s144.*
Alcantara-Licudine et al. "Analysis of phloxine B and uranine in coffee by High-performance liquid chromatography and capillary zone electrophoresis after solid phase extraction cleanup," J. Agric. Food Chem, 1998, vol. 46, pp. 1005-1011.*
Bachmann et al., "Potent stimulation and inhibition of the CFTR Cl current by phloxine B" *British Journal of Pharmacology* 131:433-440 (2000).
Cai et al., "Inhibition of the human CFTR Cl channel by the fluorescein derivative phloxine B" *Journal of Physiology* 531:124-125 (Dec. 2000).
Kaplan et al., "The potential of rose Bengal treatment used in photodynamic therapy of tumors" *Voprosy Onkologii* 45(5):557-559 (1999).

* cited by examiner

*Primary Examiner*—Shengjun Wang
(74) *Attorney, Agent, or Firm*—Bret E. Field; Bozicevic, Field & Francis LLP

(57) ABSTRACT

Fluorescein and derivatives have use in the treatment of a disease of a living animal body, including human, which disease is responsive to the inhibition of the cystic fibrosis transmembrane conductance regulator chloride channels, for instance polycystic kidney disease and secretory diarrhoea.

13 Claims, 11 Drawing Sheets

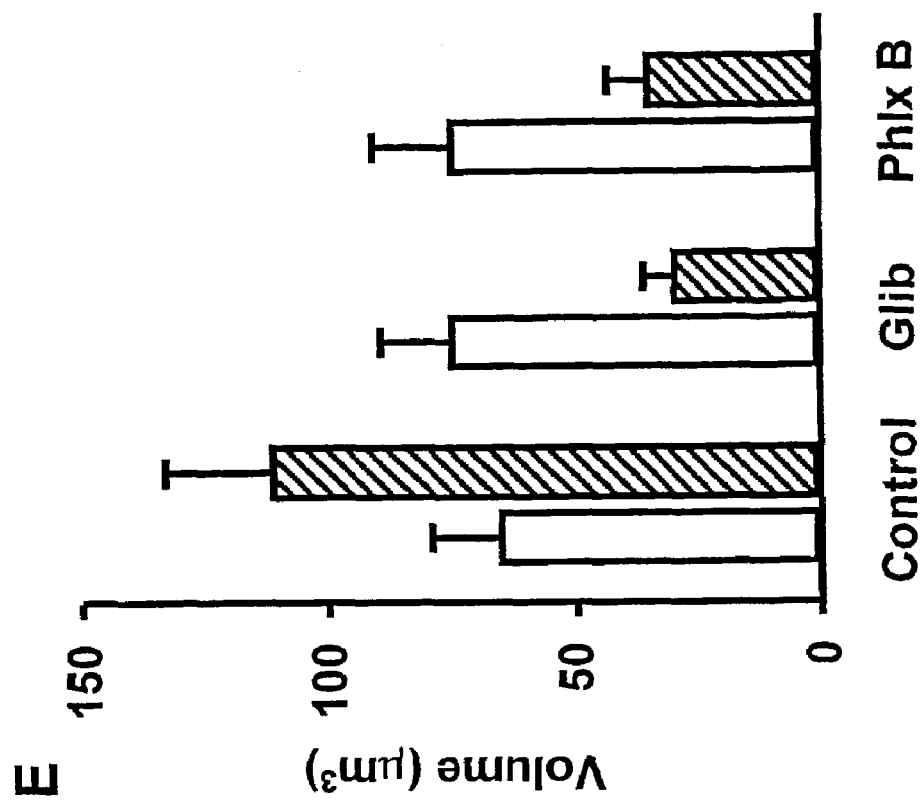
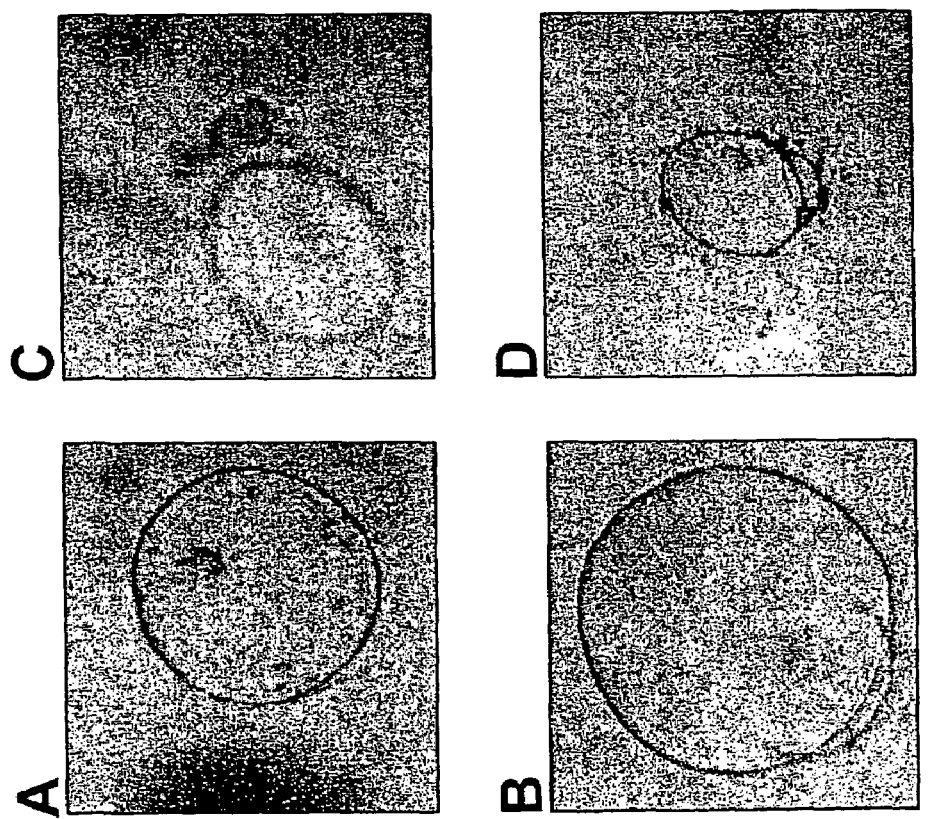
FIG. 10

INHIBITION OF THE CYSTIC FIBROSIS TRANSMEMBRANE CONDUCTANCE REGULATOR CHLORIDE CHANNEL

This application is a 371 of PCT/GB 01/03154, filed Jul. 12, 2001, which claims the foreign priority of United Kingdom application No. 0017084.5, filed Jul. 13, 2000.

The present invention relates to the inhibition of the cystic fibrosis transmembrane conductance regulator (CFTR) chloride (Cl⁻) channel. More particularly, it relates to members of a defined class of chemical compounds as blockers or inhibitors of the CFTR Cl⁻ channel and the use of these agents in the treatment of diseases caused by the malfunction of the CFTR Cl⁻ channel.

CFTR (1) forms a Cl⁻ channel with complex regulation (2, 3). It is predominantly expressed in the apical membrane of epithelia, where it provides a pathway for the movement of Cl⁻ ions and a key point at which to regulate the rate of transepithelial salt and water movement (4)

FIG. 1: REGULATION OF THE CFTR Cl⁻ CHANNEL

The domain structure of the cystic fibrosis transmembrane conductance regulator (CFTR) showing the regulation of channel gating is illustrated diagrammatically in FIG. 1. Schematic representations of channel gating are shown below the model: C, closed state; O, open state. Abbreviations: MSD, membrane-spanning domain; NBD, nucleotide-binding domain; P, phosphorylation of the R domain; PKA, cAMP-dependent protein kinase; PPase, phosphatase; R, regulatory domain, In, intracellular; Out, extracellular. The white box represents the cell membrane.

CFTR is composed of five domains: two membrane-spanning domains (MSDs), two nucleotide-binding domains (NBDs), and a regulatory (R) domain (1). The MSDs contribute to the formation of the Cl⁻-selective pore, while the NBDs and R domain control channel activity (2, 3). The activation of the cAMP-dependent protein kinase (PKA) causes the phosphorylation of multiple serine residues within the R domain. Once the R domain is phosphorylated, channel gating is controlled by a cycle of ATP hydrolysis at the NBDs.

Dysfunction of CFTR is associated with a wide spectrum of disease. Mutations, which in general, abolish the function of CFTR cause the genetic disease cystic fibrosis (CF; 4). However, some forms of male infertility, disseminated bronchiectasis, and chronic pancreatitis are also caused by mutations which, it is thought, preserve partial CFTR function (4). A greater than normal activity of the CFTR Cl⁻ channel is thought to be implicated in certain other diseases, for example polycystic kidney disease and secretory diarrhoea (5, 6).

Nucleoside triphosphates, such as ATP, control the activity of the CFTR Cl⁻ channel. Once phosphorylated by PKA, micromolar concentrations of ATP are required to regulate the opening and closing of the CFTR Cl⁻ channel. Intracellular ATP also regulates a class of K⁺ channels, termed ATP-sensitive K⁺ channels ($K_{ATP}$ channels; 7). The opening of $K_{ATP}$ channels in pancreatic β cells, myocytes, and some neurons is coupled to the cytoplasmic concentration of ATP.

In contrast to the CFTR Cl⁻ channel where ATP interacts with the NBDs to control channel gating, ATP prevents K⁺ flow through the pore of the $K_{ATP}$ channel to inhibit channel activity.

$K_{ATP}$ channels have a well-defined pharmacology. They are inhibited by sulphonylureas, a class of hypoglycaemia-inducing drugs used to treat non-insulin dependent diabetes mellitus and stimulated by a novel class of drugs called K⁺ channel openers (8). In contrast, the pharmacology of the CFTR Cl⁻ channel is less well defined. It has been demonstrated that the sulphonylureas, glibenclamide and tolbutamide, and the K⁺ channel openers, diazoxide, BRL 38227 (levcromakalim), and minoxidil sulphate inhibit cAMP-stimulated Cl⁻ currents in cells expressing wild-type human CFTR (9). The data indicated that glibenclamide is a potent inhibitor of CFTR Cl⁻ currents. It was subsequently shown that glibenclamide inhibits CFTR by occluding the intracellular end of the CFTR pore and preventing Cl⁻ permeation (10).

U.S. Pat. No. 5,234,922 discloses, as CFTR Cl⁻ channel blockers or inhibitors for use in the treatment of secretory diarrhoea, certain sulphonylurea compounds, including tolbutamide and glibenclamide. Also disclosed as having CFTR Cl⁻ channel blocking function are compounds that have activity as potassium channel openers.

Certain derivatives of the compound fluorescein have been found to modulate the activity of $K_{ATP}$ channels (11). The fluorescein derivatives were found to have two opposite effects. Firstly, they can inhibit $K_{ATP}$ channels. Secondly, they are able to reactivate $K_{ATP}$ channels that have become inactivate (termed "run-down") in the absence of cytoplasmic components required to maintain channel activity.

The present invention is based on the discovery that certain fluorescein derivatives can be used to inhibit CFTR Cl⁻ channels and, as a consequence, that these compounds have use in the treatment of a disease or condition that is responsive to the inhibition or blockade of the CFTR Cl⁻ channel, for instance polycystic kidney disease and secretory diarrhoea.

Accordingly, the present invention provides use of a compound of the formula I

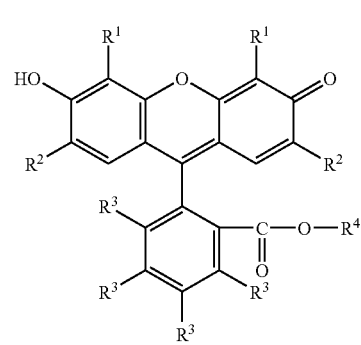

wherein $R^1$, $R^2$ and $R^3$ may each be the same or a different group selected from H, 1 to 6C alkyl and halo and $R^4$ is a group selected from H and 1 to 6C alkyl, and pharmaceutically-acceptable salts thereof, in the manufacture of a medicament for the treatment of a disease of a living animal body, including a human, which disease is responsive to the inhibition of the cystic fibrosis transmembrane conductance regulator chloride channel.

The invention further provides a method of treating a disease of a living animal body, including a human, which disease is responsive to the inhibition of the CFTR Cl⁻ channel which method comprises administering to the living animal body a CFTR Cl⁻ channel inhibiting amount of a compound of the formula I.

The fluorescein compounds that have been found to be useful in carrying out the present invention have the formula I

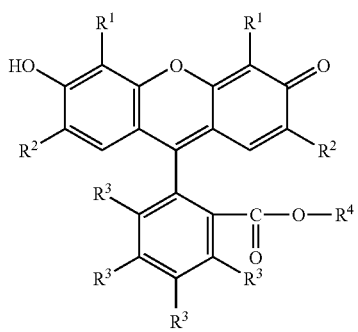

in which $R^1$, $R^2$ and $R^3$ may each be the same or a different group selected from H, 1 to 6C alkyl and halo and $R^4$ is a group selected from H and 1 to 6C alkyl groups or a pharmaceutically-acceptable salt-forming cationic group. Preferable are compounds in which $R^1$, $R^2$ and $R^3$ is the same or different group selected from H, a 1 to 4C alkyl group or pharmaceutically-acceptable salts of the carboxylic acid when $R^4$ is H. More preferable, are compounds of the formula I above in which $R^1$ is selected from H, Cl, Br and I, $R^2$ is selected from H, Cl, Br and I, $R^3$ is selected from H, Cl, Br and I and $R^4$ is selected from H, methyl and ethyl.

Fluorescein is a well-known compound. It, and its derivatives as described herein, can be synthesised according to procedures known in the art.

As mentioned above, compounds of the formula I have use as pharmaceutically-active ingredients in the treatment of an animal body, including human, suffering from a disease or condition which is responsive to the inhibition or blockade of the CFTR Cl⁻ channel. The dosage administered to the animal body in need of therapy will, of course, depend on the actual active compound used, the mode of treatment and the type of treatment required. The active compound may, of course, be administered on its own or in the form of an appropriate medicinal composition containing, for instance, an appropriate pharmaceutically-acceptable carrier or diluent. Other substances may also be present in such medicinal compositions, such as adjuvants and stabilisers the use of which is well known to persons skilled in the art. The active compound may be administered to the animal body, including human, requiring treatment by any appropriate means. Typically, administration of the active compound or medicinal preparation containing it, will be by an oral or intravenous route.

Examples of diseases or conditions which are responsive to the inhibition of the cystic fibrosis transmembrane conductance regulator chloride channels and, therefore, which may be treated by the administration to the animal body, including human, suffering from such diseases or conditions, of a CFTR chloride channel inhibiting dose of a fluorescein compound of the formula I as defined above include polycystic kidney disease, secretory diarrhoea, cardiac arrhythmia, angiogenesis and tumour vascularization. In addition, we believe that the fluorescein compounds, as defined above, also have use as male contraceptives.

BRIEF DESCRIPTION OF DRAWING

FIG. 10: Phloxine B (40 μm) inhibits cyst growth.

EXPERIMENTAL METHODS

1. Electrophysiological Experiments

Methods

Cell Culture

Figure 1:
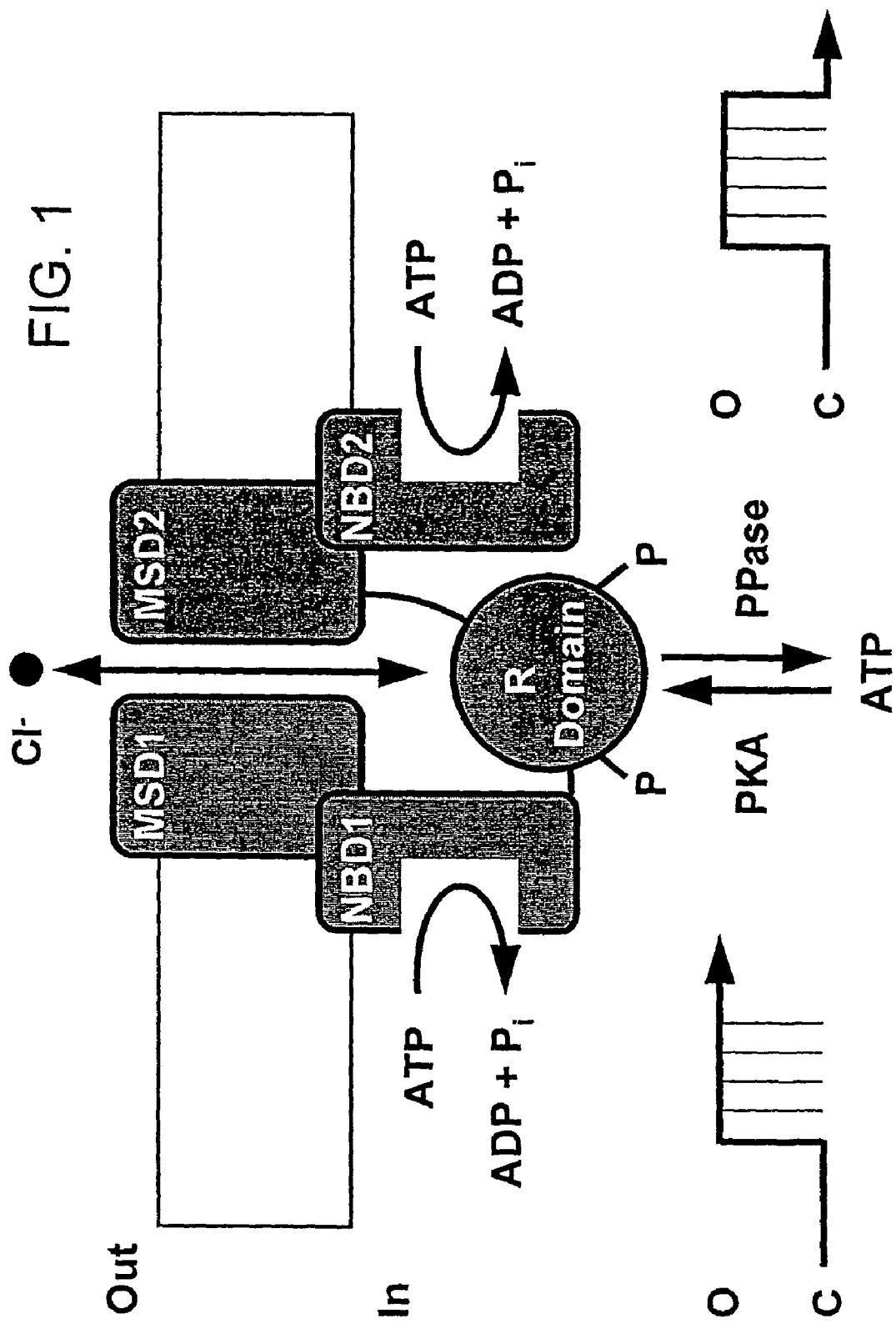
FIG. 1: Regulation of the CFTR Cl⁻ channel.

For electrophysiological experiments, we used mouse mammary epithelial cells (C127 cells) stably expressing wild-type human CFTR (12). C127 cells expressing wild-type CFTR were cultured as previously described (10). Cells were seeded onto glass coverslips and used within 48 h.

Electrophysiology

CFTR Cl⁻ channels were recorded in excised inside-out membrane patches using an Axopatch 200A patch-clamp amplifier (Axon Instruments Inc., Foster City, USA) and pCLAMP data acquisition and analysis software (version 6.03, Axon Instruments Inc.) as previously described (10, 13). The established sign convention was used throughout; currents produced by positive charge moving from intra- to extracellular solutions (anions moving in the opposite direction) are shown as positive currents.

The pipette (extracellular) solution contained (in mM): 140 N-methyl-D-glucamine (NMDG), 140 aspartic acid, 5 $CaCl_2$, 2 $MgSO_4$, and 10 N-tris[hydroxymethyl]methyl-2-aminoethanesulphonic acid (Tes), pH 7.3 with Tris ([Cl⁻], 10 mM). The bath (intracellular) solution contained (in mM): 140 NMDG, 3 $MgCl_2$, 1 ethylene glycol-bis(β-aminoethyl-ether)-N,N,N',N'-tetraacetic acid caesium salt (CsEGTA), and 10 Tes, pH 7.3 with HCl, ([Cl⁻], 147 mM; [Ca²⁺]$_{free}$, <10⁻⁸ M). All experiments were conducted at 37° C.

After excision of membrane patches from C127 cells, CFTR Cl⁻ channels were activated by the addition of the catalytic subunit of protein kinase A (PKA; 75 nM) and ATP (1.0 mM) to the intracellular solution. The ATP concentration was subsequently reduced to 0.3 mM (the EC$_{50}$ for activation of CFTR Cl⁻ channels by intracellular ATP). PKA was maintained in the intracellular solution for the duration of experiments. Unless otherwise stated, voltage was −50 mV.

To investigate the effect of phloxine B on CFTR Cl⁻ channels, we used membrane patches containing large numbers of active channels for time course studies and membrane patches containing five or less active channels for single-channel studies. The number of channels per patch was determined from the maximum number of simultaneous channel openings observed during the course of an experiment, as previously described (10). Because the effects of some fluorescein derivatives on CFTR Cl⁻ channels were only partially reversible (see Results), specific interventions were not bracketed by control periods made with the same concentration of ATP and PKA, but without fluorescein derivatives. However, we have previously shown that in the continuous presence of PKA and ATP, run-down of CFTR Cl⁻ channels in excised membrane patches from C127 cells is minimal (10).

CFTR Cl⁻ currents were initially recorded on digital audiotape using a digital tape recorder (Biologic Scientific Instruments, model DTR-1204; Intracel Ltd, Royston, UK) at a bandwidth of 10 kHz. On playback, records were filtered with an eight pole Bessel filter (Frequency Devices, model 902LPD2; Scensys Ltd, Aylesbury, UK) at a corner frequency of 500 Hz and acquired using a Digidata 1200 interface (Axon Instruments Inc.) and pCLAMP at sampling rates of either 2.5 kHz (time course studies) or 5.0 kHz (single-channel studies).

In time course studies, each point is the average current for a 4 s period with data points collected continuously; no data were collected while solutions were changed. Average current (I) for a specific intervention was determined as the average of all the data points collected during the intervention. The relationship between drug concentration and CFTR inhibition was fitted to the Hill equation:

$$I_{Drug}/I_{Control} = 1/\{1+([Drug]/K_i)^n\} \quad (1)$$

where [Drug] is the concentration of drug, $I_{Drug}/I_{Control}$ is the fractional current at the indicated drug concentration relative to that in the same solution in the absence of added drug, $K_i$ is the drug concentration causing half-maximal inhibition, and n is the slope factor (Hill coefficient). Mean data were fitted to a linear form of equation (1) using linear least-squares regression to yield $K_i$ and n values.

To measure single-channel current amplitude (i), Gaussian distributions were fitted to current amplitude histograms. For open probability (P$_o$) and kinetic analyses, lists of open and closed times were created using a half-amplitude crossing criterion for event detection. Transitions <1 ms in duration were excluded from the analyses. P$_o$ was calculated using the equation:

$$P_o = (T_1+T_2+\ldots+T_N)/(NT_{tot}), \quad (2)$$

where N is the number of channels; $T_{tot}$ is the total time analysed, and $T_1$ is the time that one or more channels are open, $T_2$ is the time two or more channels are open and so on. Only membrane patches that contained a single active channel were used for single-channel kinetic analyses.

To investigate whether inhibition of CFTR by fluorescein derivatives was voltage dependent, we used voltage ramp protocols. Macroscopic current-voltage (I-V) relationships were obtained in the absence and presence of fluorescein derivatives by averaging currents generated by 15-30 ramps of voltage each of 2 s duration; holding voltage was −50 mV. Basal currents recorded in the absence of PKA and ATP were subtracted from those recorded in the absence and presence of fluorescein derivatives to determine the effect of these agents on CFTR Cl⁻ currents.

Reagents

The catalytic subunit of PKA was purchased from Promega Ltd. ATP (disodium salt), bengal rose B, eosin Y, fluorescein, glibenclamide, phloxine B, Tes and tetrachlorofluorescein were obtained from Sigma-Aldrich Company Ltd (Poole, UK). All other chemicals were of reagent grade.

Fluorescein derivatives are based on structure I above. For fluorescein, $R^1$, $R^2$, $R^3$, and $R^4$ are H. For tetrachlorofluorescein, $R_1$, $R^2$ and $R^4$ are H and $R^3$ is Cl. For eosin Y, $R^1$ and $R^2$ are both Br and $R^3$ and $R^4$ are both H. For phloxine B, $R^1$ and $R^2$ are both Br, $R^3$ is Cl and $R^4$ is H. For bengal rose B, $R^1$ and $R^2$ are both I, $R^3$ is Cl and $R^4$ is H.

Stock solutions of fluorescein derivatives were prepared in dimethyl sulphoxide and stored at −20° C. Immediately before use, stock solutions were diluted in intracellular solution to achieve final concentrations. The vehicle did not affect the activity of CFTR Cl⁻ channels (14).

Statistics

Results are expressed as mean±SEM of n observations. To compare sets of data, we used Student's t test. Differences were considered statistically significant when P<0.05. All tests were performed using SigmaStat (version 1.03; Jandel Scientific GmbH, Erkrath, Germany).

Results

Phloxine B Modulates the Activity of CFTR Cl⁻ Currents

To examine the effect of phloxine B on wild-type human CFTR, we studied CFTR Cl⁻ currents in excised inside-out membrane patches from C127 cells stably expressing wild-type human CFTR. Addition of phloxine B to the solution bathing the intracellular side of the membrane in the absence of either ATP (n=4) or PKA (n=4) was without effect on the activity of CFTR Cl⁻ channels (data not shown). However, when phloxine B was added to the intracellular solution in the continuous presence of PKA and ATP channel activity was altered.

FIG. 2: PHLOXINE B MODULATES THE ACTIVITY OF CFTR

Time course of CFTR Cl⁻ current in an excised inside-out membrane patch from a C127 cell stably expressing wild-type CFTR. ATP (0.3 mM), PKA (75 nM), and phloxine B (Phlx B; 5-50 µM) were present in the intracellular solution during the times indicated by the bars. Voltage was −50 mV, and there was a Cl⁻ concentration gradient across the membrane (internal $[Cl^-]$=147 mM; external $[Cl^-]$=10 mM). Each point is the average current for a 4 s period and no data were collected while solutions were changed. For the purpose of illustration, the time course has been inverted so that an upward deflection represents an inward current.

Figure 2:
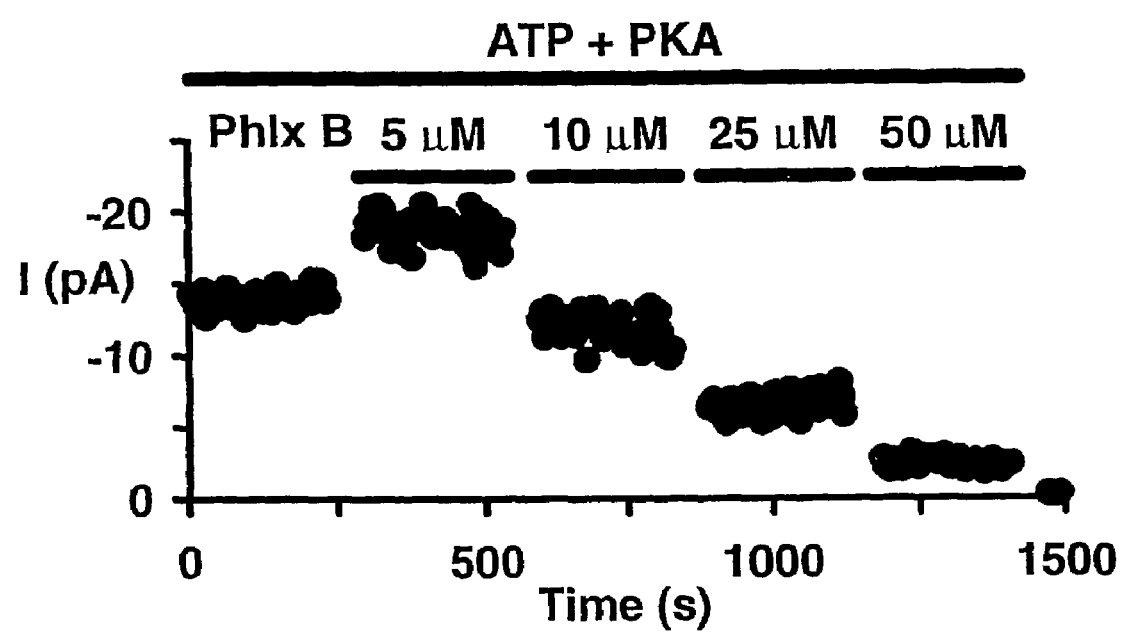
FIG. 2: Phloxine B modulates the activity of CFTR.

FIG. 2 demonstrates that phloxine B modulates the activity of CFTR Cl⁻ currents. Addition of phloxine B (1-5 µM) to the intracellular solution stimulated CFTR Cl⁻ currents. In contrast, higher concentrations of phloxine B (20-50 µM) caused a concentration-dependent decrease in CFTR Cl⁻ current.

In addition to phloxine B, we tested other fluorescein derivatives, including fluorescein, tetrachlorofluorescein, eosin Y, and bengal rose B.

FIG. 3: CONCENTRATION-RESPONSE RELATIONSHIPS OF FLUORESCEIN DERIVATIVES

A, data are means±SEM; n =3-9 observations at each concentration. Fluorescein derivatives are indicated by different symbols (bengal rose B, circles; phloxine B, squares; eosin Y, triangles; tetrachlorofluorescein, diamonds; fluorescein, hexagons). Values above the dotted line indicate stimulation of CFTR, whereas values below the line indicate inhibition. B, Hill plots of CFTR inhibition by phloxine B, eosin Y and tetrachlorfluorescein for the data shown in A. The continuous lines are the fit of first order regressions to the data. For phloxine B, $K_i$=17 µM and n=2; for eosin Y, $K_i$=48 µM and n=1.6; and for tetrachlorofluorescein, $K_i$=58 µM and n=0.7. Other details as in FIG. 2.

Figure 3:
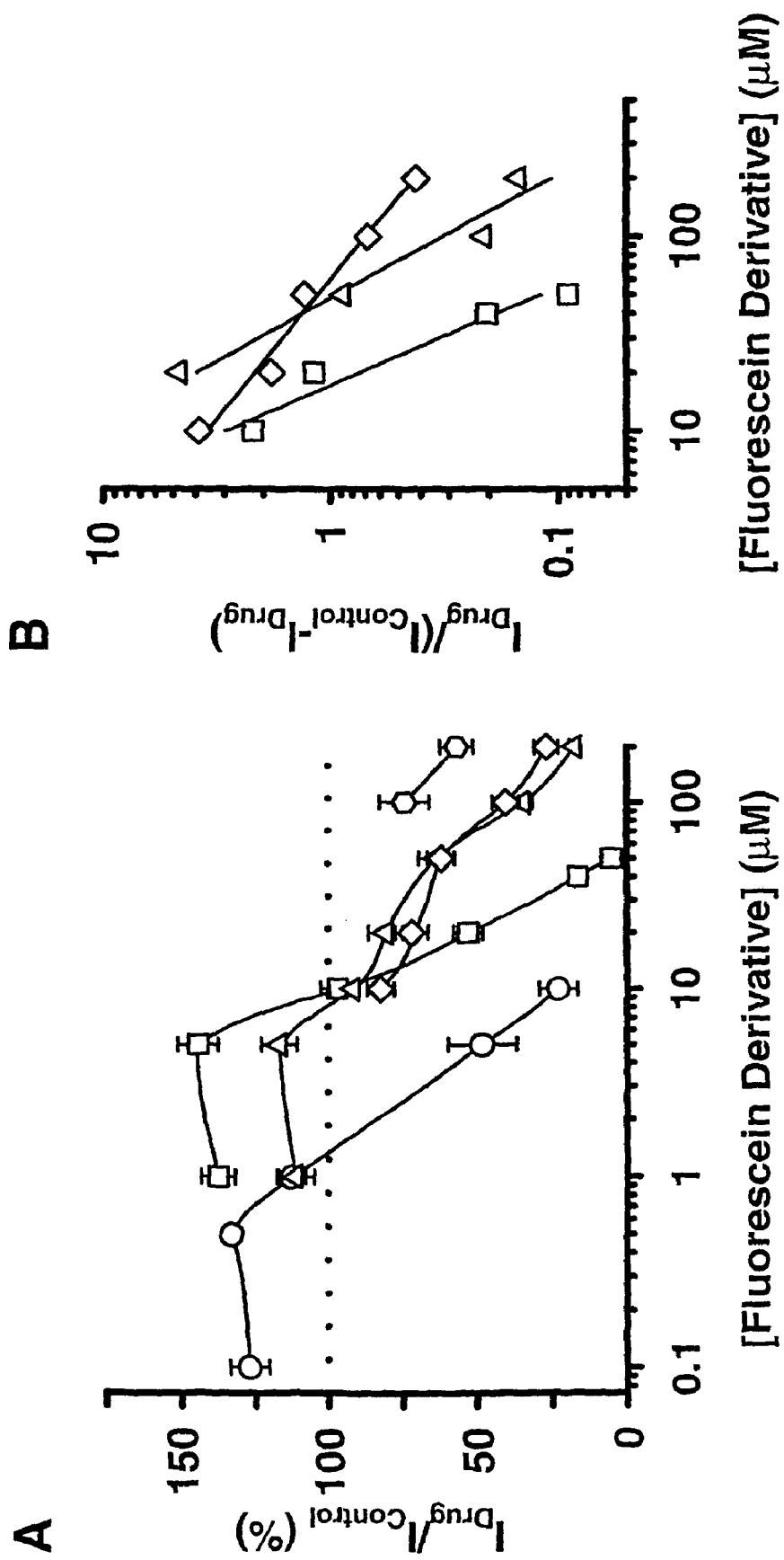
FIG. 3: Concentration-response relationships of Fluorescein derivatives.
Figure 6:
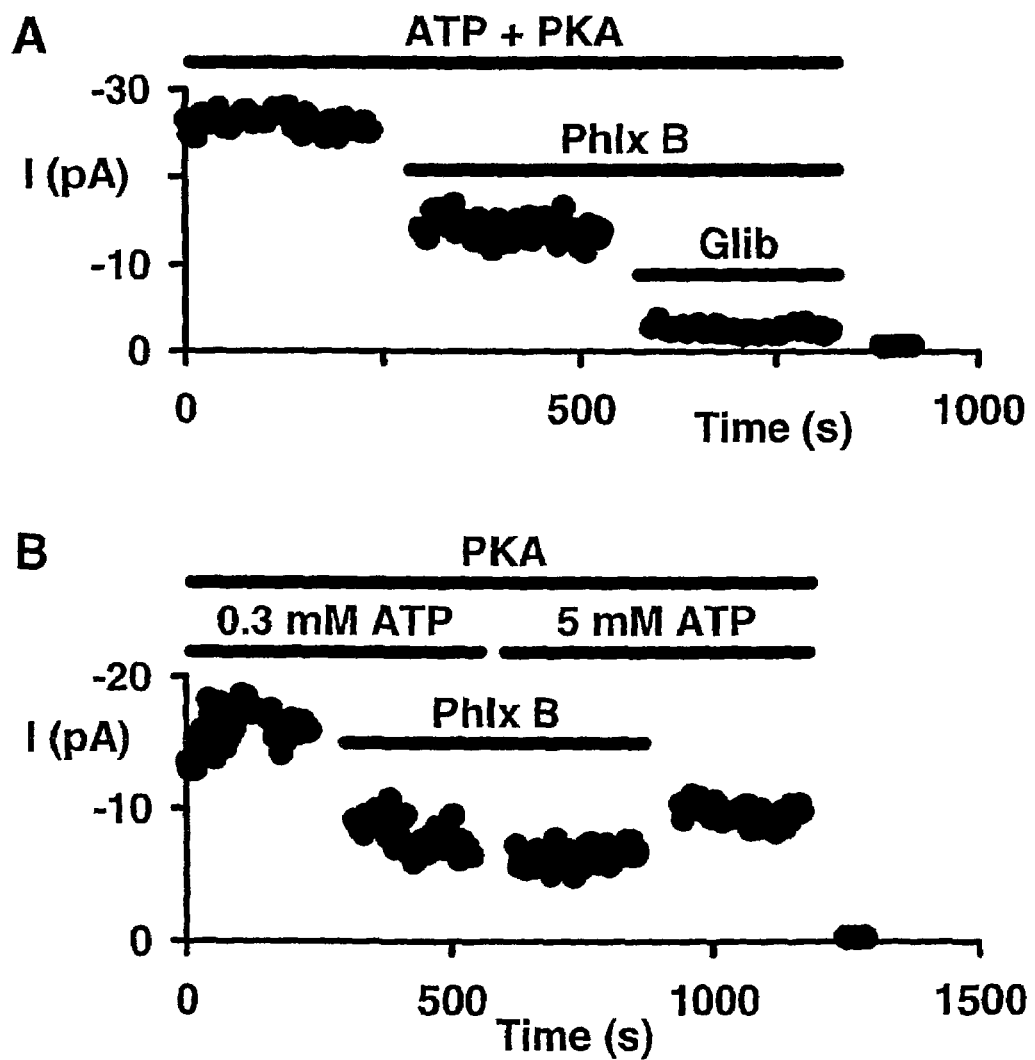
FIG. 6: Effect of glibenclamide and ATP on phloxine B inhibition of CFTR.

FIG. 3 demonstrates that fluorescein derivatives modulated the activity of the CFTR Cl⁻ channel. All the fluorescein derivatives tested inhibited channel activity, whereas only eosin Y, phloxine B and bengal rose B stimulated channel activity. The rank order of potency for CFTR inhibition was bengal rose B>phloxine B>eosin Y≧tetrachlorofluorescein>>fluorescein. Inhibition of CFTR by eosin Y was readily reversible (n=7; data not shown). In contrast, inhibition by phloxine B and tetrachlorofluorescein were partially reversible (n=3-6; FIG. 6 and data not shown) and inhibition by bengal rose B was irreversible (n=3; data not shown).

FIG. 3B demonstrates that for eosin Y, phloxine B and tetrachlorofluorescein the relationship between drug concentration and current inhibition was well fitted by the Hill equation. These data suggest fluorescein derivatives are potent blockers of the CFTR Cl⁻ channel. Bengal rose B and phloxine B inhibit CFTR with potency greater than or equal to that of glibenclamide, a widely used blocker of the CFTR Cl⁻ channel (9). Eosin Y and tetrachlorofluorescein inhibit CFTR less potently than glibenclamide, but more potently than many other blockers of the CFTR Cl⁻ channel including the arylaminobenzoates, diphenylamine-2-carboxylate (DPC) and 5-nitro-2-(3-phenylpropylamino)-benzoic acid (NPPB), the disulphonic stilbenes, 4,4'-dinitrostilbene-2,2'-disulphonic acid (DIDS) and 4,4'-dinitrostilbene-2,2'-disulphonic acid (DNDS) and the flavonoid, genistein (15-18).

Interestingly, the data also suggest that phloxine B and eosin Y inhibit CFTR by binding at two sites that interact co-operatively, whereas tetrachlorofluorescein binds to a single site to inhibit CFTR.

Mechanism of Phloxine B Inhibition of CFTR

Previous studies have demonstrated that some agents inhibit CFTR by binding within the CFTR pore to prevent Cl⁻ permeation, whereas other drugs inhibit CFTR by greatly slowing the rate of channel opening (18-20). To investigate how phloxine B inhibits CFTR, we tested the effect of phloxine B (20 µM) on the single-channel activity of CFTR using membrane patches that contained ≦5 active channels.

FIG. 4: PHLOXINE B (20 µM) INHIBITS THE SINGLE-CHANNEL ACTIVITY OF CFTR

A, representative recordings show the effect of phloxine B (20 µM) on the activity of three CFTR Cl⁻ channels. ATP (0.3 mM) and PKA (75 nM) were continuously present in the intracellular solution. Voltage was −50 mV, and there was a Cl⁻ concentration gradient across the membrane (internal $[Cl^-]$=147 mM; external $[Cl^-]$=10 mM). Dashed lines indicate the closed channel state and downward deflections correspond to channel openings. Traces on the left are 20 s long; the 1 s portions indicated by the bars are shown on an expanded time scale to the right. B and C, effect of phloxine B on I and $P_o$, respectively. Columns and error bars indicate means±SEM; n=6 observations at each concentration. The asterisks indicate values that are significantly different from the control value (P<0.05). Other details as in A.

Figure 4:
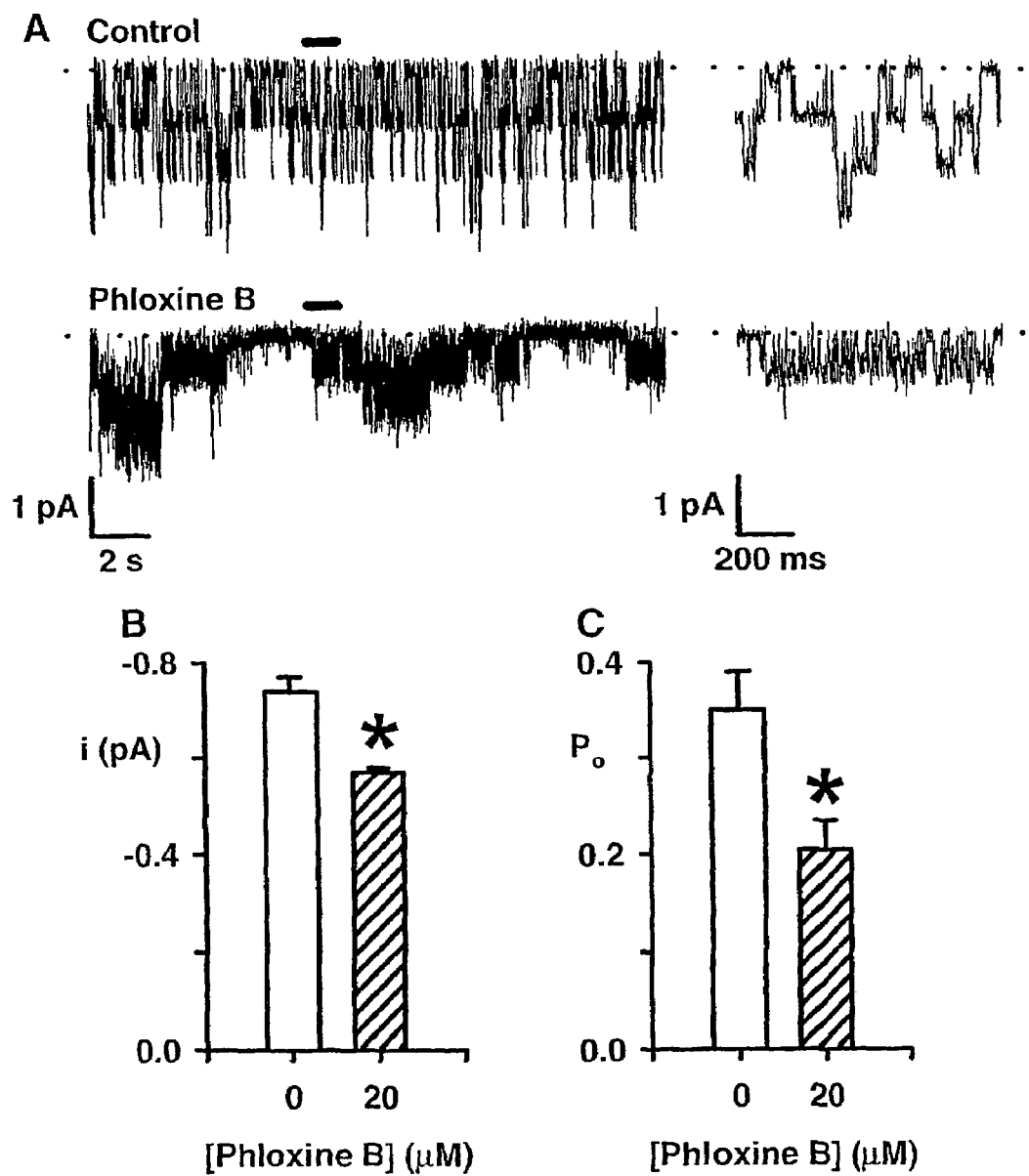
FIG. 4: Phloxine B (20 μm) inhibits the single-channel activity of CFTR.

FIG. 4A shows the effect of phloxine B (20 µM) on the activity of three CFTR Cl⁻ channels following phosphorylation by PKA. Visual inspection of these traces suggests that phloxine B (20 µM) dramatically altered the pattern of channel gating. The pattern of gating of wild-type CFTR is characterised by bursts of activity interrupted by brief flickery closures separated by longer closures between bursts (FIG. 4A, top traces). Phloxine B (20 µM) altered the gating behaviour of CFTR in three ways. First, it greatly prolonged the closed-time interval between bursts (FIG. 4A). Second, it caused a large increase in flickery closures interrupting bursts of channel activity (FIG. 4A). Third, it appeared to prolong the duration of bursts (FIG. 4A). To quantify these effects, we measured i and $P_o$. FIGS. 4B and C shows that phloxine B (20 µM) significantly decreased both i and $P_o$(P<0.05).

We also tested the effect of eosin Y, tetrachlorofluorescein and bengal rose B on the single-channel activity of CFTR.

Figure 5:
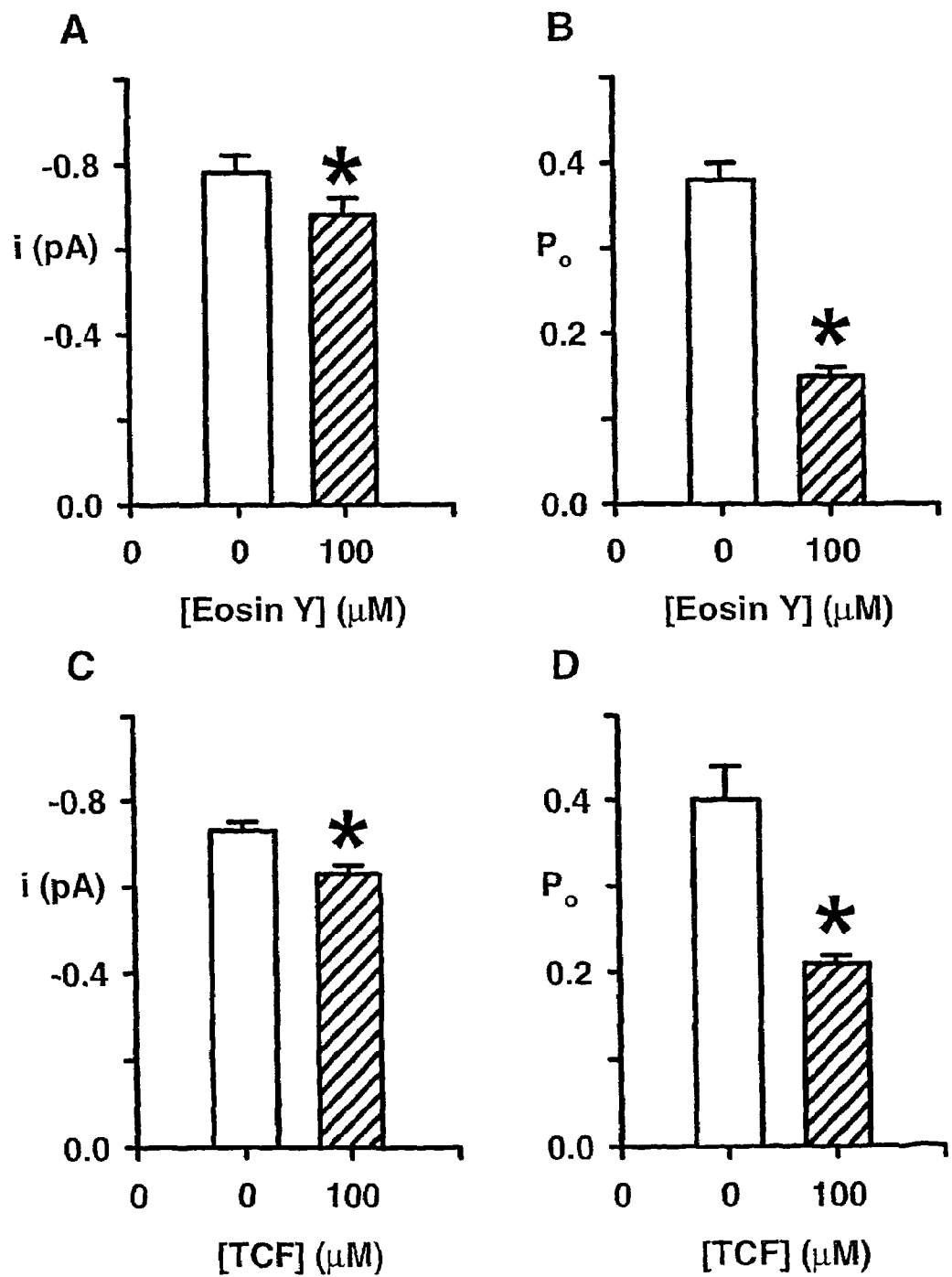
FIG. 5: Eosin Y and tetrachlorofluorescein inhibition of the single-channel activity of CFTR.

FIG. 5: EOSIN Y AND TETRACHLOROFLUORESCEIN INHIBITION OF THE SINGLE-CHANNEL ACTIVITY OF THE CFTR

Left, effect of fluorescein derivatives on i. Right, effect of fluorescein derivatives on $P_o$. A and B, eosin Y (100 µM) and C and D, tetrachlorofluorescein (TCF; 100 µM). Columns and error bars indicate means±SEM; n=6-7 observations at each concentration. The asterisks indicate values that are significantly different from the control value (P<0.05). Other details as in FIG. 4.

FIG. 5 demonstrates that eosin Y (100 μM) and tetrachlorofluorescein (100 μM) inhibited channel activity by decreasing both i and $P_o$. In the presence of bengal rose B (10 μM) we were never able to resolve discrete channel openings, suggesting that it dramatically decreased i and/or $P_o$ (n=3, data not shown).

Fluorescein derivatives inhibit glibenclamide binding to $K_{ATP}$ channels (11). Based on these data, we were interested to test the effect of phloxine B on glibenclamide inhibition of CFTR Cl⁻ channels.

FIG. 6: EFFECT OF GLIBENCLAMIDE AND ATP ON PHLOXINE B INHIBITION OF CFTR

A and B, time-courses of CFTR Cl⁻ current showing the effect of glibenclamide and ATP concentration, respectively, on phloxine B inhibition of CFTR. During the times indicated by the bars ATP (0.3 or 5 mM), PKA (75 nM), phloxine B (20 μM), and glibenclamide (Glib; 50 μM) were present in the intracellular solution. Other details as in FIG. 2.

Stimulation of CFTR with phloxine B (1 μM) failed to prevent channel block by glibenclamide (50 μM; n=5, data not shown). Moreover, FIG. 6A demonstrates that glibenclamide (50 μM) potentiated channel block by phloxine B (20 μM). Phloxine B (20 μM) decreased I to 59±4% of the control value (n=5), whereas phloxine B (20 μM) and glibenclamide (50 μM) decreased 1 to 10±2% of the control value (n=5; P<0.001).

Elevated concentrations of the CFTR activators 5'-adenylylimidodiphosphate (AMP-PNP) and genistein inhibit channel activity by greatly slowing the rate of NBD1-mediated channel opening (18, 19, 21). Like genistein, (18, 21), phloxine B prolonged the duration of long closures separating channel openings. This suggests that genistein and phloxine B might inhibit the CFTR Cl⁻ channel by similar mechanisms. To test this idea, we investigated whether high concentrations of ATP attenuate phloxine B inhibition of CFTR. In contrast to genistein block of CFTR (21), FIG. 6B demonstrates that ATP (5 mM) fails to relieve phloxine B (20 μM) inhibition of CFTR Cl⁻ currents. In the presence of ATP (0.3 and 5 mM), phloxine B (20 μM) decreased 1 to 56±6% and 51±5% of the control value, respectively (n=6; P>0.05). Similarly, CFTR inhibition by eosin Y (100 μM) was unaffected by elevated concentrations of ATP (n=5; data not shown).

The prolonged channel openings interrupted by flickery closures induced by inhibitory concentrations of phloxine B suggest that phloxine B might be an open-channel blocker of CFTR. To investigate this idea, we examined the voltage-dependence of channel inhibition. Membrane patches were bathed in symmetrical 147 mM Cl⁻ solutions and CFTR Cl⁻ currents recorded in the absence and presence of phloxine B (40 μM) over the voltage range±100 mV using a voltage ramp protocol.

Figure 7:
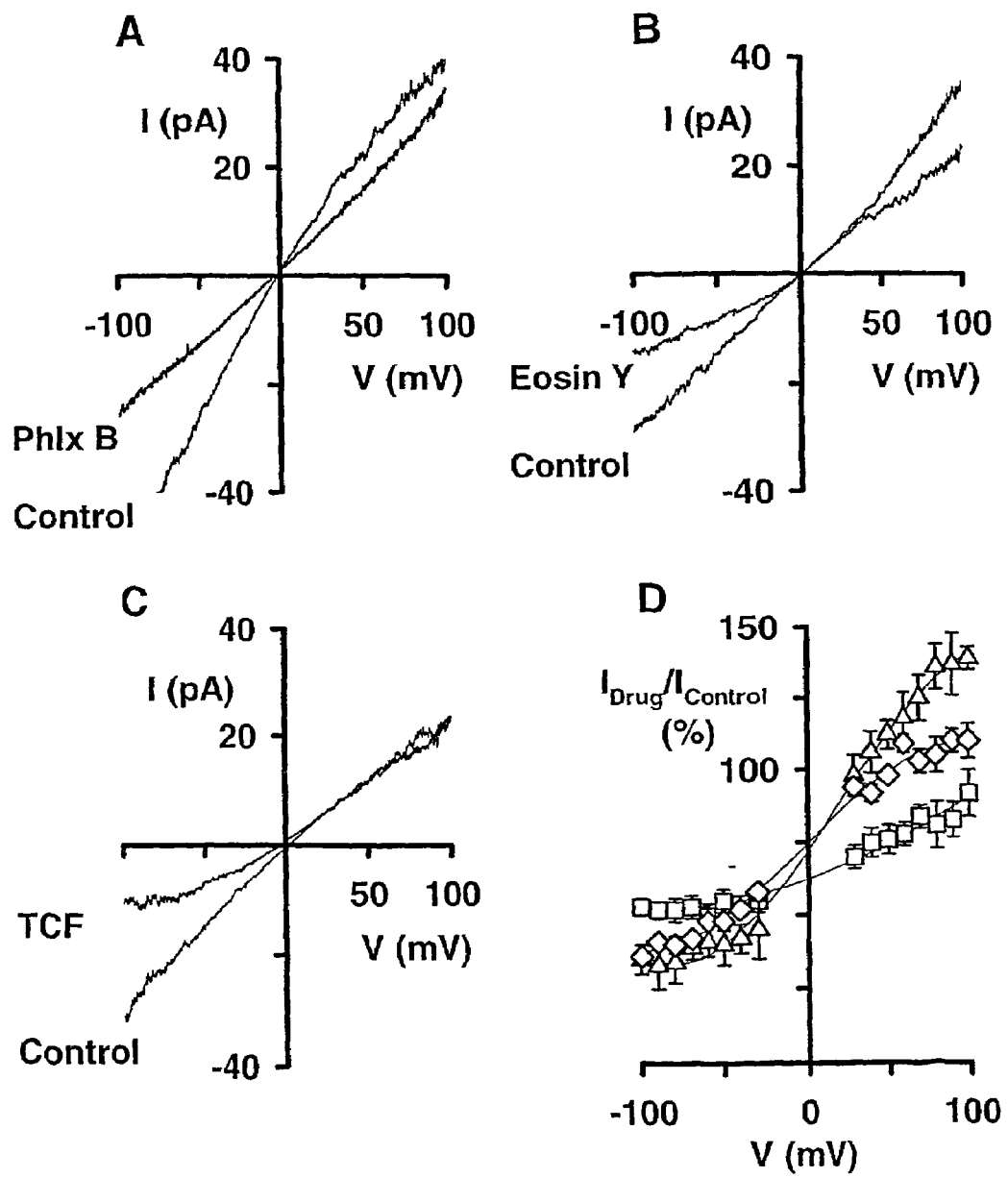
FIG. 7: Voltage-dependence of phloxine B, eosin Y and tetrachlorofluorescein inhibition of CFTR Cl⁻ currents.

FIG. 7: VOLTAGE-DEPENDENCE OF PHLOXINE B, EOSIN Y AND TETRACHLOROFLUORESCEIN INHIBITION OF CFTR Cl⁻ CURRENTS

A, B and C, I-V relationships of CFTR Cl⁻ currents recorded in the absence and presence of phloxine B (40 μM), eosin Y (100 μM) and tetrachlorofluorescein (100 μM), respectively, when the membrane patch was bathed in symmetrical 147 mM Cl⁻ solutions. ATP (1 mM) and PKA (75 nM) were continuously present in the intracellular solution. I-V relationships were generated as described in the Methods; holding voltage was −50 mV. D, effect of voltage on the fraction of CFTR Cl⁻ current inhibited by phloxine B (40 μM, squares), eosin Y (100 μM, triangles) and tetrachlorofluorescein (100 μM, diamonds). Values are means±SEM (n=5-6) at each voltage.

FIGS. 7A-D demonstrates that CFTR inhibition by the fluorescein derivatives phloxine B, eosin Y and tetrachlorofluorescein is voltage-dependent. At negative voltages, phloxine B (40 μM), eosin Y (100 μM) and tetrachlorofluorescein (100 μM) decreased CFTR Cl⁻ currents. At positive voltages, channel block by phloxine B (40 μM) and tetrachlorofluorescein (100 μM) was relieved and eosin Y (100 μM) stimulated channel activity. Thus, the data indicate that CFTR inhibition by the fluorescein derivatives phloxine B, eosin Y and tetrachlorofluorescein is voltage-dependent and unaffected by changes in ATP concentration. They also suggest that the location of the phloxine B binding site might be distinct from that of glibenclamide.

Discussion

Our data indicate that fluorescein derivatives, such as phloxine B, inhibit the CFTR Cl⁻ channel. The data suggest that they inhibit CFTR in two ways: slowing channel opening and blocking open channels. They also suggest that phloxine B and bengal rose B inhibit CFTR with equal or greater potency than glibenclamide, a widely used inhibitor of CFTR (9, present study).

A number of agents that stimulate CFTR Cl⁻ channels have been demonstrated to inhibit channel activity at high concentrations. These include AMP-PNP (19) genistein (18, 21) and pyrophosphate (22). Each of these agents stimulates CFTR Cl⁻ channels by binding tightly to NBD2, slowing greatly the rate of NBD2-mediated channel closure, and hence, prolonging dramatically the duration of bursts of channel activity (18, 23, 24).

The characteristics of CFTR inhibition by fluorescein derivatives showed some similarities to those of AMP-PNP and genistein. AMP-PNP and genistein block the CFTR Cl⁻ channel by suppressing strongly NBD1-mediated channel opening (18, 19, 21). In addition, genistein occludes weakly the CFTR pore (21). Both genistein and phloxine B caused a flickery block that prolonged the duration of bursts and lengthened dramatically the closed-time interval between bursts (18, 21, present study). However, ATP (5 mM) and voltage had markedly different effects on channel block by these agents. Genistein inhibition was voltage-independent and relieved by ATP (5 mM; 21). In contrast, phloxine B inhibition was voltage-dependent, but unaffected by ATP (5 mM) (present study). The failure of ATP (5 mM) to relieve phloxine B inhibition of CFTR was not a consequence of the slow dissociation of the drug from the channel because we observed identical results using eosin Y, a fluorescein derivative that dissociates rapidly from CFTR (n=5, data not shown). Our observation that inhibition of CFTR by fluorescein derivatives is voltage-dependent indicates that these drugs bind within the electric field of the membrane. Although it is feasible that fluorescein derivatives might block CFTR by an allosteric mechanism, the simplest interpretation of the data is that these drugs bind within the CFTR pore to prevent $Cl^-$ permeation (20). This suggests that both the phloxine B-induced flickery block of channel openings and the prolonged closed-time interval between bursts are caused by phloxine B occlusion of the CFTR pore.

The discovery that fluorescein derivatives potently inhibit CFTR $Cl^-$ channels has implications for the treatment of diseases associated with the dysfunction of CFTR. Fluorescein derivatives that strongly inhibit CFTR $Cl^-$ channels are believed to have value in the treatment of diseases, such as polycystic kidney disease and secretory diarrhoea, which may involve increased activity of the CFTR $Cl^-$ channel (5, 6). Because, CFTR is expressed in cardiac myocytes and endothelial cells (2, 25), inhibitors of CFTR might also be used to prevent cardiac arrhythmias, angiogenesis, and tumour vascularization.

2. Cyst Growth Experiments

Methods

Cell Culture

For cyst growth and cell proliferation experiments, we used Type I Madin-Darby canine kidney (MDCK) cells. We chose Type I MDCK cells because they form cysts when grown in collagen gels in the presence of cAMP agonists (26) and because they express the CFTR $Cl^-$ channel (27). MDCK cells were cultured in MDCK media (a 1:1 mixture of Dulbecco's Modified Eagle Medium (DMEM) and Ham's F-12 nutrient medium supplemented with 100 U $ml^{-1}$ penicillin, and 100 µg $ml^{-1}$ streptomycin and either 10% fetal bovine serum (FBS; cyst growth) or 5% FBS and 1% insulin-transferrin-selenium-X (ITS-X) supplement (cell proliferation); all from Life Technologies Ltd, Paisley, UK) at 37° C. in a humidified atmosphere of 5% $CO_2$.

Cyst Growth

To grow cysts, MDCK cells were cultured in collagen gels using a modification of the method of Grantham et al. (26). Cells were trypsinized with 0.25% (wt/vol) trypsin for 30 minutes at 37° C., diluted with MDCK media containing 10% FBS to form a suspension of between $1-3 \times 10^4$ cells $ml^{-1}$, and aliquoted into individual wells of a 24-well plate (0.1 ml per well). Each well contained 0.4 ml of ice-cold Vitrogen (3.0 mg $ml^{-1}$ collagen; Cohesion Technologies Inc., Palo Alto, USA) supplemented with 10% (vol/vol) 10× minimum essential medium, 10 mM N-[2-hydroxyethyl] piperazine-N'-[2-ethanesulphonic acid] (Hepes), 27 mM $NaHCO_3$, 100 U $ml^{-1}$ penicillin, and 100 µg $ml^{-1}$ streptomycin, and adjusted to pH 7.4 with NaOH. The 24-well plate was gently agitated to distribute cells throughout the Vitrogen and incubated in a water bath at 37° C. for 90 minutes to promote gelation of the Vitrogen.

After gelation, 1.5 ml MDCK media containing 10% FBS was added to each well of the 24-well plate. To promote cyst growth, we added cAMP agonists (forskolin (10 µM), 3-isobutyl-1-methylxanthine (IBMX; 100 µM), and 8-(4-chlorophenylthio) adenosine 3':5'-cyclic monophosphate (CPT-cAMP; 500 µM)) to the MDCK media. Plates were maintained at 37° C. in a humidified atmosphere of 5% $CO_2$ and the MDCK media containing cAMP agonists changed every three days.

Twelve days after seeding collagen gels with MDCK cells, cysts were readily detected at ×1000 magnification using an inverted microscope with phase contrast optics (Leica, model DMIL, Milton Keynes, UK). To test the effect of CFTR modulators on cyst growth, drugs were added to MDCK media in the continued presence of cAMP agonists. MDCK media containing cAMP agonists and CFTR modulators was changed every 3 days for a total period of 9 days. Photographs of individual cysts were taken before the addition of CFTR modulators and at three day intervals over the duration of the experiment. To identify individual cysts, each cyst was assigned a unique reference number using a grid placed below the 24-well plate.

Cyst Volume Measurement

The diameter of cysts was measured directly from photographs of cysts using images that had been magnified by identical amounts. By assuming that cysts are spherical in shape, we calculated cyst volume ($\frac{4}{3} \cdot \pi \cdot r^3$).

Cell Proliferation

To test the effect of CFTR modulators on the proliferation of MDCK cells, we used Type I MDCK cells grown in media containing 5% FBS and 1% ITS-X supplement. On day −1, MDCK cells were seeded at $7.5 \times 10^4$ cells $ml^{-1}$ in 35 mm dishes containing MDCK media with 1% FBS and 1% ITS-X supplement. On day 0, the concentration of FBS was reduced further to 0.01% and CFTR modulators added to the MDCK media. MDCK media containing CFTR modulators was changed every 2 days for a total period of 6 days. To determine the number of cells per 35 mm dish, Type I MDCK cells were harvested using trypsin (0.25% wt/vol), centrifuged at 1200 rpm for 5 min and resuspended in 1 ml of MDCK media before counting using a haemocytometer.

Reagents

Bumetanide, CPT-cAMP, DIDS, forskolin, genistein, glibenclamide, Hepes, IBMX, ouabain and phloxine B were purchased from the Sigma-Aldrich Company Ltd. (Poole, UK). NPPB was obtained from Semat Technical (UK) Ltd. (St. Albans, UK). The chemical structure of phloxine B is indicated above. All other chemicals were of reagent grade.

CPT-cAMP was dissolved in distilled water, forskolin in methanol, and IBMX in ethanol; all other drugs were dissolved in DMSO. Stock solutions were stored at −20° C. and diluted in MDCK media to achieve final concentrations immediately before use. Precautions against light-sensitive reactions were observed when using bumetanide, ouabain, and CFTR modulators. The vehicle, DMSO, was without effect on cyst growth (control, 112±20% increase between days 12 and 21; n=29; DMSO (0.4% v/v), 99±36% increase between days 12 and 21; n=8; P>0.5) and cell proliferation (n=8; P>0.05).

To check the efficacy of DIDS, we added DIDS to the intracellular side of excised inside-out membrane patches and tested its effect on the CFTR $Cl^-$ channel. Consistent with the data of Linsdell and Hanrahan (17), DIDS (200 µM) potently inhibited the activity of CFTR (n=3; data not shown).

Statistics

Results are expressed as means±SEM of n observations. To compare sets of data, we used either Student's t test or the Mann-Whitney rank sum test. Differences were considered statistically significant when P<0.05. All tests were performed using SigmaStat™ (version 1.03, Jandel Scientific GmbH, Erkrath, Germany).

Results

We first observed cysts 3-6 days after seeding collagen gels with MDCK cells and incubating these cells in culture media containing cAMP agonists (forskolin (10 µM), IBMX (100 µM) and CPT-cAMP (500 µM)).

Figure 8:
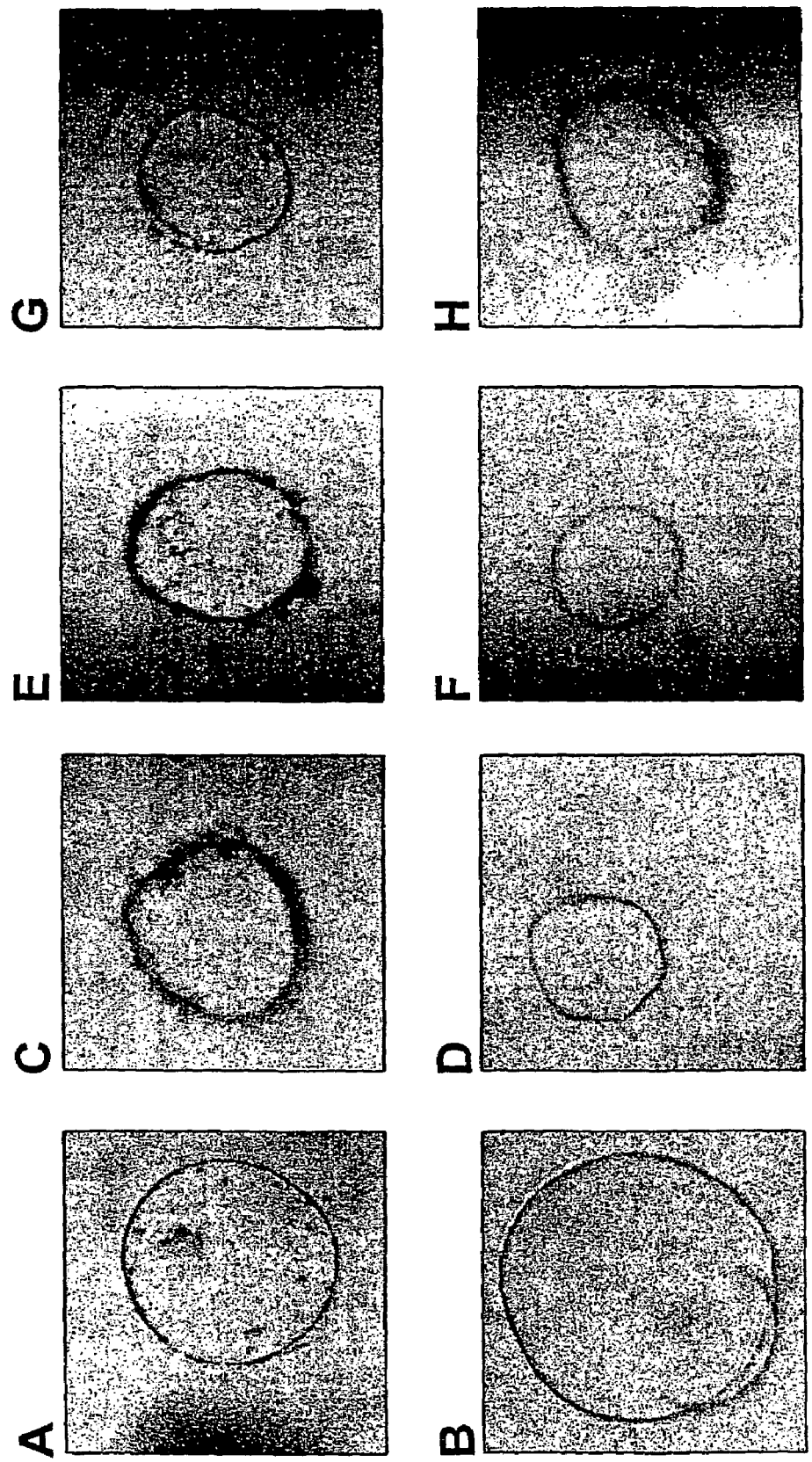
FIG. 8: Phase-contrast images of cysts before (A, C, E, and G) and after (B, D, F, and H) treatment with CFTR inhibitors.

FIG. 8: PHASE-CONTRAST IMAGES OF CYSTS BEFORE (A, C, E, AND G) AND AFTER (B, D, F, AND H) TREATMENT WITH CFTR INHIBITORS

A and B, control. C and D, glibenclamide (100 µM). E and F, NPPB (400 µM). G and H, DIDS (200 µM). Micrographs were taken on day 12 (A, C, E, and G) and day 21 (B, D, F, and H) after seeding collagen gels with MDCK cells. Bar=200 µm.

Cysts progressively increased in size and by day 12 they were readily detected at ×100 magnification using an inverted microscope with phase contrast optics (FIG. 8A). In the sustained presence of cAMP agonists, cysts continued to enlarge. FIGS. 8A and B demonstrates that there was a visible increase in cyst size between days 12 and 21. Over this time interval, cyst volume increased by 112±20% (n=29). Based on these data, we examined the effect of CFTR blockers on cyst growth between days 12 and 21.

We tested the effect on cyst growth of the sulphonylurea, glibenclamide, the arylaminobenzoate, NPPB, and the flavonoid, genistein. Glibenclamide and NPPB inhibit the CFTR $Cl^-$ channel by preventing the permeation of $Cl^-$ ions through the CFTR pore (10, 16), whereas genistein inhibits the CFTR $Cl^-$ channel by greatly slowing the rate of channel opening (18, 21). As a control, we tested the effect on cyst growth of the disulphonic stilbene, DIDS. When added to the extracellular side of the membrane, DIDS is without effect on the CFTR $Cl^-$ channel (28). This distinguishes CFTR from other epithelial $Cl^-$ channels that are inhibited by extracellular DIDS (28). FIGS. 8C-F demonstrates that there was a visible decrease in the size of cysts treated with glibenclamide (100 µM) and NPPB (400 µM). Similar results were obtained with genistein (100 µM; data not shown). In contrast, DIDS (200 µM) was without effect on cyst growth (FIGS. 8G and H).

To quantify the effect of inhibitors of the CFTR $Cl^-$ channel on cyst growth, we measured cyst volume. As controls, we tested the effect on cyst volume of ouabain and bumetanide, two agents that inhibit cyst growth (26). Ouabain inhibits the $Na^+$-$K^+$-ATPase and bumetanide blocks the $Na^+$-$K^+$-$2Cl^-$ co-transporter.

FIG. 9: CFTR BLOCKERS INHIBIT CYST GROWTH

Data show the effect on cyst volume of ouabain (1 µM), bumetanide (bumet; 100 µM), glibenclamide (glib; 100 µM), NPPB (400 µM), genistein (100 µM) and DIDS (200 µM); control cysts were untreated. The open and shaded columns represent cyst volumes measured on days 12 and 21, respectively. Values are means±SEM (n=23-30 cysts from 4-5 experiments) for each drug.

Figure 9:
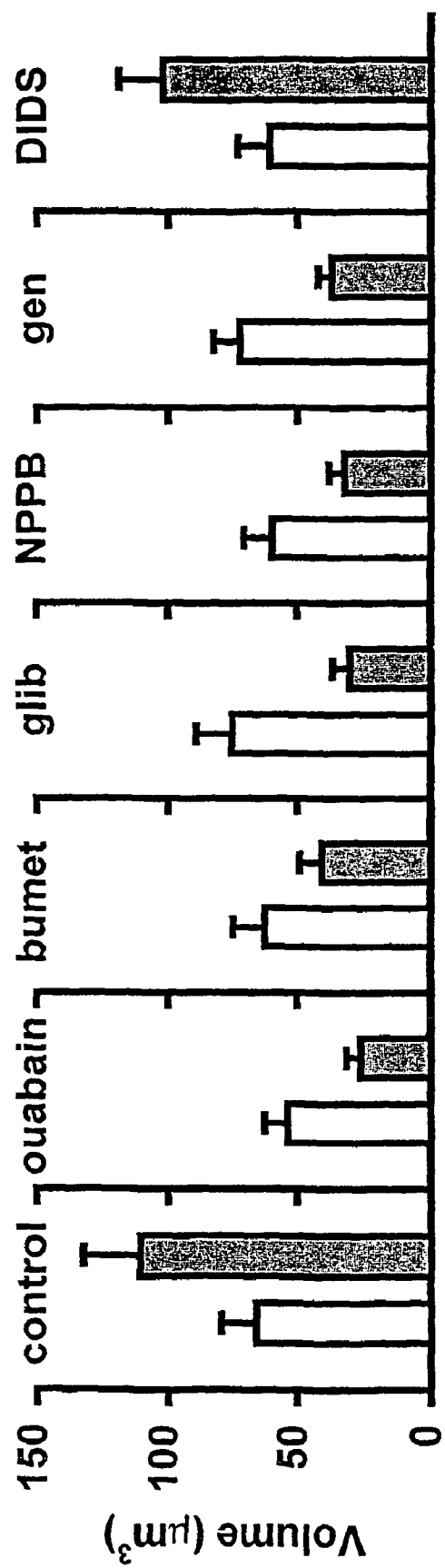
FIG. 9: CFTR blockers inhibit cyst growth.

FIG. 9 shows that the volume of control cysts increased significantly between days 12 and 21 after seeding collagen gels with MDCK cells (P<0.001). With the exception of DIDS (200 µM; P>0.5), all the inhibitors tested decreased cyst volume, with glibenclamide (100 µM)≧ouabain (1 µM)≧NPPB (400 µM)≧genistein (100 µM)>bumetanide (100 µM; P<0.001; FIG. 9).

Our data indicate that blockers of the CFTR $Cl^-$ channel inhibit cyst growth. Based on these data, we speculated that fluorescein derivatives might inhibit cyst growth. To test this hypothesis, we investigated the effect of phloxine B.

FIG. 10: PHLOXINE B (40 µM) INHIBITS CYST GROWTH

A-D, phase-contrast images of MDCK cysts before (A and C) and after (B and D) treatment with phloxine B (40 µM). A and B control. C and D phloxine B (40 µM). Micrographs were taken on day 12 (A and C) and day 21 (B and D) after seeding collagen gels with MDCK cells. Bar=200 µM. E, effect of phloxine B (40 µM) and glibenclamide (100 µM) on the volume of MDCK cysts. The open and hatched columns represent cyst volumes measured on days 12 and 21, respectively. Values are mean±SEM; n=29-30 cysts from 5 experiments. Control and glibenclamide data are from FIGS. 8 and 9.

FIGS. 10 A-D shows phase-contrast photomicrographs of cysts grown in the absence and presence of phloxine B (40 µM) on days 12 and 21 after seeding collagen gels with MDCK cells. In the absence of phloxine B, cysts increased in size (FIGS. 10A and B). In contrast, in the presence of phloxine B (40 µM), there was a visible decrease in the size of cysts (FIGS. 10C and D). The mean decrease in cyst volume was similar to that of glibenclamide (100 µM), a potent inhibitor of the CFTR $Cl^-$ channel and cyst growth (9; FIG. 10E).

In polycystic kidney disease, the development and growth of cysts involves the proliferation of immature epithelial cells, changes in the extracellular matrix and the accumulation of fluid within the cyst cavity (5). Because blockers of the CFTR $Cl^-$ channel inhibited cyst growth without increasing the thickness of cyst walls (FIGS. 8 and 10), we speculated that these agents might inhibit both fluid accumulation and cell proliferation. To test the effect of inhibitors of the CFTR Cl⁻ channel on cell proliferation, we used Type I MDCK cells.

FIG. 11: CFTR BLOCKERS INHIBIT THE PROLIFERATION OF MDCK CELLS

Data show the time course of cell proliferation of (A) control (filled circles), glibenclamide (100 µM; open circles, ), phloxine B (40 µM; open squares) and DIDS (200 µM; open triangles); (B) control (filled circles), ouabain (1 µM; open circles) and bumetanide (100 µM; open squares); (C) control (filled circles), cAMP agonists (forskolin (10 µM), IBMX (100 µM) and CPT-cAMP (500 µM); open circles), NPPB (400 µM; open squares) and genistein (100 µM; open triangles). Values are means±SEM (n=6-10) observations at each time point. Error bars are smaller than symbol size, except where shown.

Figure 11:
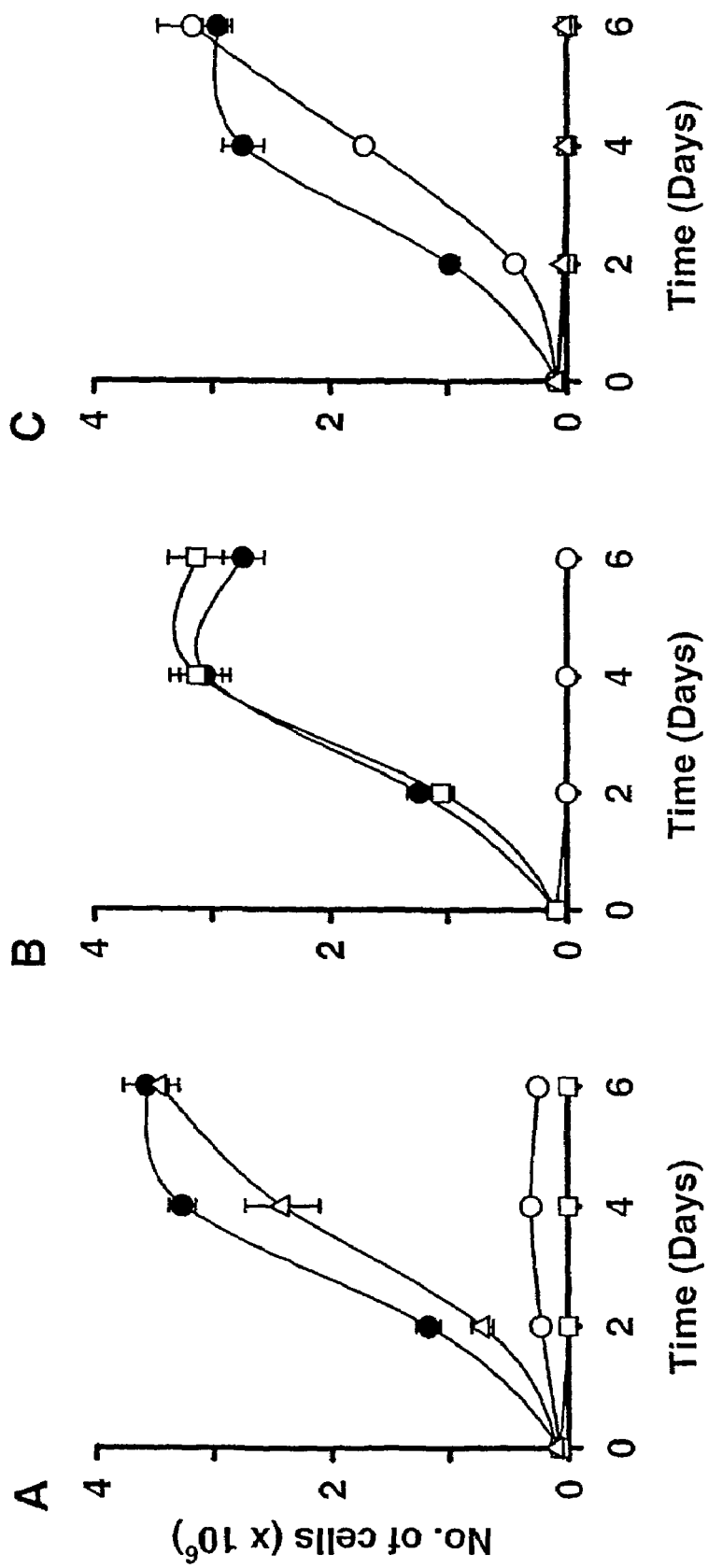
FIG. 11: CFTR blockers inhibit the proliferation of MDCK cells.

FIG. 11 demonstrates that blockers of the CFTR Cl⁻ channel inhibit the proliferation of Type I MDCK cells. Between day 0 and 6 there was a large increase in the number of control cells. With the exception of DIDS (200 µM) and bumetanide (100 µM), all the inhibitors tested prevented cell growth with ouabain (1 µM)=phloxine B (40 µM)=genistein (100 µM)=NPPB (400 µM)>glibenclamide (100 µM). Like phloxine B, bengal rose B (5 µM), eosin Y (200 µM) and tetrachlorofluorescein (200 µM) inhibited the proliferation of Type I MDCK cells (n=3-8; data not shown).

Previous work has shown that cAMP agonists may either stimulate or inhibit the growth of cells (29). FIG. 11C demonstrates that cAMP agonists slowed the growth of type I MDCK cells. However, at day 6, the number of cells in the presence of cAMP agonists did not differ from that of the control (P>0.05; FIG. 11C). Inhibition of cell growth by the CFTR blockers was unaffected by cAMP agonists (glibenclamide and phloxine B (n=7-8); NPPB and genistein (n=2); data not shown).

Discussion

Our data demonstrate that blockers of the CFTR Cl⁻ channel inhibit cyst growth. Like the CFTR Cl⁻ channel (10, 16, 18, present study), glibenclamide, NPPB, and high concentrations of genistein and phloxine B inhibited cyst enlargement and cell proliferation. In contrast, DIDS, an agent that inhibits other epithelial Cl⁻ channels, but not CFTR (28), was without effect on cyst growth and cell proliferation.

Our data have important implications for the treatment of polycystic kidney disease. At present, there are no cures for the disorder. Instead, patients with polycystic kidney disease are treated with drugs to manage pain, infection, and hypertension (30). However, once renal failure develops, long-term dialysis and kidney transplantation are required to preserve the lives of patients with polycystic kidney disease (30). In search of new therapies for polycystic kidney disease, previous studies have investigated the effect on cyst growth of agents that inhibit cell proliferation. For example, paclitaxel (Taxol) dramatically slowed the progression of polycystic kidney disease in cpk mice (31). However, in other rodent models of the disorder paclitaxel was without effect (32). Our observation that blockers of the CFTR Cl⁻ channel retard cyst growth highlights the therapeutic potential of CFTR inhibitors in the treatment of polycystic kidney disease. By slowing cyst growth, therapeutically-active inhibitors of CFTR might prevent the destruction of the architecture of the kidney and hence, preserve renal function. Such drugs would enhance greatly the quality of life of patients with polycystic kidney disease.

References

1. Riordan, J. R., J. M. Rommens, B. -S. Kerem, N. Alon, R. Rozmahel, Z. Grzelczak, J. Zielenski, S. Lok, N. Plavsic, J. -L. Chou, M. L. Drumm, M. C. lannuzzi, F. S. Collins, and L. -C. Tsui. 1989. Identification of the cystic fibrosis gene: cloning and characterization of complementary DNA. *Science* 245:1066-1073.
2. Gadsby, D. C. and A. C. Nairn. 1999. Control of cystic fibrosis transmembrane conductance regulator channel gating by phosphorylation and nucleotide hydrolysis. *Physiological Reviews* 79 (Supplement 1):S77-S107.
3. Sheppard, D. N. and M. J. Welsh. 1999. Structure and function of the cystic fibrosis transmembrane conductance regulator chloride channel. *Physiological Reviews* 79 (Supplement 1):S23-S45.
4. Welsh, M. J., L. -C. Tsui, T. F. Boat, and A. L. Beaudet. 1995. Cystic fibrosis. In The Metabolic and Molecular Basis of inherited Disease. C. R. Scriver, A. L. Beaudet, W. S. Sly, and D. Valle, editors. McGraw-Hill Inc. New York. 3799-3876.
5. Sullivan, L. P., D. P. Wallace, and J. J. Grantham. 1998. Epithelial transport in polycystic kidney disease. *Physiological Reviews* 78:1165-1191.
6. Gabriel, S. E., K. N. Brigman, B. H. Koller, R. C. Boucher, and M. J. Stutts. 1994. Cystic fibrosis heterozygote resistance to cholera toxin in the cystic fibrosis mouse model. *Science* 266:107-109.
7. Ashcroft, F. M. and F. M. Gribble. 1998. Correlating structure and function in ATP-sensitive $K^+$ channels. *Trends in Neurosciences* 21:288-294.
8. Edwards, G. and A. H. Weston. 1993. The pharmacology of ATP-sensitive potassium channels. *Annual Review of Pharmacology and Toxicology* 33:597-637.
9. Sheppard, D. N. and M. J. Welsh. 1992. Effect of ATP-sensitive $K^+$ channel regulators on cystic fibrosis transmembrane conductance regulator chloride currents. *Journal of General Physiology* 100:573-591.
10. Sheppard, D. N. and K. A. Robinson. 1997. Mechanism of glibenclamide inhibition of cystic fibrosis transmembrane conductance regulator Cl⁻ channels expressed in a murine cell line. *Journal of Physiology* 503:333-346.
11. de Weille, J. R., M. Müller, and M. Lazdunski. 1992. Activation and inhibition of ATP-sensitive $K^+$ channels by fluorescein derivatives. *Journal of Biological Chemistry* 267:4557-4563.
12. Marshall, J., S. Fang, L. S. Ostedgaard, C. R. O'Riordan, D. Ferrara, J. F. Amara, H. Hoppe IV, R. K. Scheule, M. J. Welsh, A. E. Smith, and S. H. Cheng. 1994. Stoichiometry of recombinant cystic fibrosis transmembrane conductance regulator in epithelial cells and its functional reconstitution into cells in vitro. *Journal of Biological Chemistry* 269:2987-2995.
13. Hamill, O. P., A. Marty, E. Neher, B. Sakmann, and F. J. Sigworth. 1981. Improved patch-clamp techniques for high-resolution current recording from cells and cell-free membrane patches. *Pflügers Archiv* 391:85-100.

14. Lansdell, K. A., J. F. Kidd, S. J. Delaney, B. J. Wainwright, and D. N. Sheppard. 1998. Regulation of murine cystic fibrosis transmembrane conductance regulator Cl⁻ channels expressed in Chinese hamster ovary cells. *Journal of Physiology* 512:751-764.
15. McCarty, N. A., S. McDonough, B. N. Cohen, J. R. Riordan, N. Davidson, and H. A. Lester. 1993. Voltage-dependent block of the cystic fibrosis transmembrane conductance regulator Cl⁻ channel by two closely related arylaminobenzoates. *Journal of General Physiology* 102: 1-23.
16. Walsh, K. B., Long, K. J., and Shen, X. 1999. Structural and ionic determinants of 5-nitro-2-(3-phenylpropylamino)-benzoic acid block of the CFTR chloride channel. *British Journal of Pharmacology* 127:369-376.
17. Linsdell, P. and J. W. Hanrahan. 1996. Disulphonic stilbene block of cystic fibrosis transmembrane conductance regulator Cl⁻ channels expressed in a mammalian cell line and its regulation by a critical pore residue. *Journal of Physiology* 496:687-693.
18. Wang, F., S. Zeltwanger, l. C. -H. Yang, A. C. Naim, and T. -C. Hwang. 1998. Actions of genistein on cystic fibrosis transmembrane conductance regulator channel gating: evidence for two binding sites with opposite effects. *Journal of General Physiology* 111 :477-490.
19. Mathews, C. J., J. A. Tabcharani, and J. W. Hanrahan. 1998. The CFTR chloride channel: nucleotide interactions and temperature-dependent gating. *Journal of Membrane Biology* 163:55-66.
20. Hwang, T. -C. and D. N. Sheppard. 1999. Molecular pharmacology of the CFTR Cl⁻ channel. *Trends in Pharmacological Sciences* 20:448-453.
21. Lansdell, K. A., Z. Cai, J. F. Kidd, and D. N. Sheppard. 2000. Two mechanisms of genistein inhibition of cystic fibrosis transmembrane conductance regulator Cl⁻ channels. *Journal of Physiology* 524:317-330.
22. Ma, J., J. Zhao, M. L. Drumm, J. Xie, and P. B. Davis. 1997. Function of the R domain in the cystic fibrosis transmembrane conductance regulator chloride channel. *Journal of Biological Chemistry* 272:28133-28141.
23. Hwang, T. -C., G. Nagel, A. C. Naim, and D. C. Gadsby. 1994. Regulation of the gating of cystic fibrosis transmembrane conductance regulator Cl channels by phosphorylation and ATP hydrolysis. *Proceedings of the National Academy of Sciences USA* 91:4698-4702.
24. Carson, M. R., M. C. Winter, S. M. Travis, and M. J. Welsh. 1995. Pyrophosphate stimulates wild-type and mutant cystic fibrosis transmembrane conductance regulator Cl⁻ channels. *Journal of Biological Chemistry* 270: 20466-20472.
25. Tousson, A., B. A. Van Tine, A. P. Naren, G. M. Shaw, and L. M Schwiebert 1998. Characterization of CFTR expression and chloride channel activity in human endothelia. *American Journal of Physiology* 275:C1555-C1564.
26. Grantham, J. J., M. Uchic, E. J. Cragoe Jr, J. Kornhaus, J. A. Grantham, V. Donoso, R. Mangoo-Karim, A. Evan, and J. McAteer. 1989. Chemical modification of cell proliferation and fluid secretion in renal cysts. *Kidney International* 35:1379-1389.
27. Mohamed, A., Ferguson, D., Seibert, F. S., Cai, H. -M., Kartner, N., Grinstein, S., Riordan, J. R., and Lukacs, G. L. 1997. Functional expression and apical localization of the cystic fibrosis transmembrane conductance regulator in MOCK I cells. *Biochemical Journal* 322:259-265.
28. Schultz, B. D., A. K. Singh, D. C. Devor, and R. J. Bridges. 1999. Pharmacology of CFTR chloride channel activity. *Physiological Reviews* 79 (Supplement 1):S109-S144.
29. Dumont, J. E., Jauniaux, J. -C., and Roger, P. P. 1989. The cyclic AMP-mediated stimulation of cell proliferation. *Trends in Biochemical Sciences* 14:67-71.
30. Gabow, P. A. 1993. Autosomal dominant polycystic kidney disease. *New England Journal of Medicine* 329: 332-342.
31. Woo, D. D. L., S. Y. P. Miao, J. C. Pelayo, and A. S. Woolf. 1994. Taxol inhibits progression of congenital polycystic kidney disease. *Nature* 368:750-753.
32. Martinez, J. R., B. D. Cowley, V. H. Gattone,II, S. Nagao, T. Yamaguchi, S. Kaneta, H. Takahashi, and J. J. Grantham. 1997. The effect of paclitaxel on the progression of polycystic kidney disease in rodents. *American Journal of Kidney Diseases* 29:435-444.

The invention claimed is:

1. A method of treating a subject for a disease which is polycystic kidney disease or secretory diarrhoea, wherein said subject is known to have said disease, which method comprises administering to said subject Phloxine B as the active ingredient.

2. A method according to claim 1, wherein the disease to be treated is polycystic kidney disease.

3. A method according to claim 1, wherein the disease to be treated is secretory diarrhoea.

4. A method of treating a subject for a disease which is polycystic kidney disease or secretory diarrhoea, wherein said subject is known to have said disease, said method consisting essentially of:

administering to said subject an effective amount of a compound of the formula I

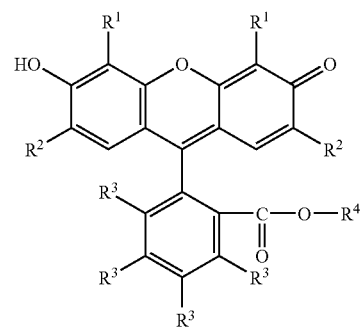

wherein each of $R^1$, $R^2$ and $R^3$, which may be the same or different, is selected from H, 1 to 6C alkyl and halo and $R^4$ is a group selected from H and 1 to 6C alkyl, and pharmaceutically-acceptable salts thereof.

5. A method according to claim 4, wherein the compound has the formula I in which $R^1$, $R^2$ and $R^3$ is the same or different and is selected from H, Cl, Br and I and $R^4$ is selected from H and 1 to 4C alkyl, and pharmaceutically-acceptable salts.

6. A method according to claim 5, wherein the compound has the formula I in which $R^1$ is selected from H, Cl, Br and I; $R^2$ is selected from H, Cl, Br and I; $R^3$ is selected from H, Cl, Br and I and $R^4$ is selected from H, methyl and ethyl.

7. A method according to claim 6, wherein the compound has the formula I in which $R^1$ and $R^2$ are both Br, $R^3$ is Cl and $R^4$ is H.

8. A method according to claim 6, wherein the compound has the formula I in which $R^1$ and $R^2$ are both I, $R^3$ is Cl and $R^4$ is H.

9. A method according to claim 6, wherein the compound has the formula I in which $R^1$, $R^2$ and $R^4$ are H and $R^3$ is Cl.

10. A method according to claim 6, wherein the compound has the formula I in which $R^1$ and $R^2$ are both Br and $R^3$ and $R^4$ are both H.

11. A method according to claim 6, wherein the compound has the formula I in which $R^1$, $R^2$, $R^3$ and $R^4$ are H.

12. A method according to claim 4, wherein the disease to be treated is polycystic kidney disease.

13. A method according to claim 4, wherein the disease to be treated is secretory diarrhoea.

* * * * *